United States Patent [19]

Sugimoto

[11] 4,383,035

[45] May 10, 1983

[54] PROCESS FOR THE PRODUCTION OF HUMAN LUTEINIZING HORMONE

[75] Inventor: Kaname Sugimoto, Okayama, Japan

[73] Assignee: Kabushiki Kaisha Hayashibara Seibutsu Kagaku Kenkyujo, Okayama, Japan

[21] Appl. No.: 290,862

[22] Filed: Aug. 7, 1981

[30] Foreign Application Priority Data

Aug. 27, 1980 [JP] Japan .................. 55-116943

[51] Int. Cl.$^3$ ...................... C12P 21/02; C12P 21/04; C12P 21/00
[52] U.S. Cl. ....................................... 435/70; 435/68; 435/71
[58] Field of Search ............................ 435/68, 70, 71

[56] References Cited

U.S. PATENT DOCUMENTS 4,276,282  6/1981  Sugimoto et al. .
4,285,929  8/1981  Sugimoto et al. .
4,288,546  9/1981  Narasimhan et al. ................. 435/70
4,328,207  5/1982  Sugimoto .

OTHER PUBLICATIONS

Chemical Abstracts, 91:86930s (1979).

Primary Examiner—Sam Rosen
Attorney, Agent, or Firm—Browdy and Neimark

[57] ABSTRACT

The present invention relates to a process for the production of human luteinizing hormone (hLH).

More precisely, the invention relates to a process for the mass production of hLH, comprising in vivo multiplication of human cells capable of producing hLH, using non-human warm-blooded animal, and exposure of the multiplied human cells to a luteinizing hormone inducer.

The hLH production according to the invention is extremely higher, in terms of hLH production per cell, than that attained by conventional processes using in vitro tissue culture, thus, hLH can be used in a sufficient amount in the prevention and treatment of human diseases.

9 Claims, No Drawings

PROCESS FOR THE PRODUCTION OF HUMAN LUTEINIZING HORMONE

DETAILED DESCRIPTION OF THE INVENTION

The present invention relates to a process for the production of human luteinizing hormone (human lutropin, abbreviated hLH hereinafter).

The hLH is a hormone, produced by the anterior lobe of the pituitary gland, which stimulates the secretion of androgen in the male, and estrogen and progestron in the female.

No process for the mass production of low-cost hLH has been established so far.

The present inventor has investigated processes for the mass production of hLH. These efforts have resulted in the unexpected finding that human cells capable of producing hLH multiplying rapidly in non-human warm-blooded animals, and have an extremely higher hLH producibility per cell than that obtained by in vitro tissue culture; up to about 2–50-folds of the latter in terms of hLH production per cell.

More precisely, the present invention relates to a process for the production of hLH, characterized in multiplying human cells capable of producing hLH by transplanting said cells to a non-human warm-blooded animal body, or alternatively multiplying said cells by allowing said cells to multiply with a device by which the nutrient body fluid of a non-human warm-blooded animal is supplied to said cells, and exposing the cells multiplied by either of the above multiplication procedures to a luteinizing hormone inducer to induce hLH.

The process according to the present invention, besides realizing a greater hLH production, requires no, or much less, nutrient medium containing expensive serum for cell multiplication, and renders the maintenance of the culture medium during the cell multiplication much easier than in the case of in vitro tissue culture. Particularly, any human cells capable of producing hLH can be multiplied easily while utilizing the nutrient body fluid supplied from the non-human warm-blooded animal by transplanting said cells to the animal body, or suspending said cells in a diffusion chamber devised to receive nutrient body fluid from the animal body, and feeding the animal in the usual way. Also, the process is characterized by stabler and higher cell multiplication, and higher hLH production per cell.

As to the human cells usable in the present invention, any human cells can be used so far as they produce hLH, and multiply easily in the non-human warm-blooded animal body. For example, conveniently feasible for use in the present invention are human cells which inherently produce hLH, such as human basophile cells from the anterior lobe of the pituitary gland, such basophile cells which have been transformed with EB virus or X-ray irradiation, or human basophile adenoma cells from a patient suffering from basophile adenoma of the pituitary gland; human lung carcinoma cells which produce ectopic hLH; and established cell lines of the above human cells. Furthermore, there may be used easily maintainable established human lymphoblastoid lines in which there has been introduced hLH production governing genetic sites by means of genetic recombination techniques using enzymes such as DNA ligase, nuclease and DNA polymerase, or by cell fusion using agents such as polyethylene glycol or Sendai virus. The use of such established human lymphoblastoid lines in which have been introduced hLH production genetic sites conveniently results in a remarkably higher cell multiplication when the cells are transplanted to a non-human warm-blooded animal body, i.e., about 2–10-fold or more higher hLH production per cell. Furthermore, since transplantation of the above mentioned established human lymphoblastoid lines to the animal body results in the formation of easily disaggregatable massive tumor, and said massive tumor is hardly contaminated with the host animal cells, the multiplied live human lymphoblastoid cells can be harvested easily.

As to the animals usable in the present invention, any animals can be used so far as the cells multiply therein. For example, poultry, such as chicken or pigeon, or a mammalian, such as dog, cat, monkey, goat, pig, cow, horse, rabbit, guinea pig, rat, hamster, mouse or nude mouse, is advantageously usable in the invention. Since such cell transplantation elicits undesirable immunoreaction, the use of a newborn or infant animal, or those in the youngest possible stage, for example, egg, embryo or foetus, is desirable. In order to reduce the immunoreaction, prior to the cell transplantation, the animal may be treated with X-ray or $\gamma$-ray irradiation, about 200–600 rem, or injection of antiserum or immunosuppressive agent prepared according to conventional methods. Since nude mice, used as the non-human warm-blooded animal, exhibit weaker immunoreaction, even when in their adulthood, conveniently, any established human cell line can be transplanted and multiplied rapidly therein without such pretreatment.

Stabilized cell multiplication and enhancement of hLH production can both be carried out by repeated transplantation using combination(s) of different non-human warm-blooded animals; for example, the objectives are attainable first by implanting said cells in hamster and multiplying therein, then by reimplanting in nude mouse. Further, the repeated transplantation may be carried out with animals of the same class or division as well as those in the same species or genus.

As to where the human cells are implantable, the human cells can be implanted in any site of the animal so far as the cells multiply therein, for example, in allantoic cavity, or intravenously, intraperitoneally, or subcutaneously.

Besides direct cell transplantation to the animal body, any known established human cell line capable of producing hLH can be multiplied easily while utilizing the nutrient body fluid supplied from the animal body by embedding, for example, intraperitoneally, in the animal body a conventional diffusion chamber, of any of various shapes and sizes, and equipped with a membrane filter, ultra filter or hollow fiber having pore sizes of about $10^{-7}$ to $10^{-5}$ m in diameter, which prevents contamination with the host cells into the diffusion chamber and allows the animal to supply the cells with its nutrient body fluid. Additionally, the diffusion chamber can be designed, if necessary, so it could be placed, for example, on the host animal, and the body fluid allowed to circulate from the animal body into the chamber, to enable the observation of the cell suspension in the chamber through transparent side window(s), equipped on the chamber wall(s), and to enable replacement and exchange with a fresh chamber; cell multiplication thereby increases to a further higher level over the period of the animal life, and the production per animal is further augmented without any sacrifice of the host animal. Furthermore, when such a diffusion chamber is used, since the multiplied human cells can be harvested easily, and no immunoreaction is elicited due to the absence of direct contact of the human cells with the host animal cells, any non-human warm-blooded animal can be used as the host in the present invention without any pretreatment to reduce the immunoreaction.

Feeding of the host animal implanted with the human cells can be carried out easily by conventional methods even after the cell transplantation, and no special care is required.

Maximum cell multiplication is attained about 1-20 weeks after the cell transplantation. When the established human cell line implanted in the animal is human tumor cell or human lymphoblastoid line, maximum cell multiplication is attained within one to five weeks after the cell transplantation due to their extremely higher cell multiplication rates.

According to the present invention, the number of the human cells obtained per host ranges from about $10^7$ to $10^{12}$ or more. In other words, the number of human cells implanted in the animal body increases about $10^2$–$10^7$-fold or more, or about $10^1$–$10^6$-fold or more than that attained by in vitro tissue culture methods using nutrient medium; thus, the cells are conveniently usable for hLH production.

As to the method for hLH induction, any method can be employed so far as the human cells obtained by the above mentioned procedure release hLH thereby. For example, the multiplied human cells, obtained by multiplying in ascite in suspension and harvesting from said ascite, or by extracting the massive tumor formed subcutaneously and harvesting after the disaggregation of the massive tumor, are suspended to give a concentration of about $10^4$ to $10^8$ cells per ml in a nutrient medium, kept at a temperature of about 20°-40° C., and then subjected to a luteinizing hormone inducer at this temperature for about one to 50 hours to induce hLH.

Preferable luteinizing hormone inducers are amino acids such as lysine, arginine, tryptophan, leucine and casamino acid; inorganic salts such as sodium chloride, potassium chloride, calcium chloride and magnesium sulfate; and hormone such as luteinizing hormone releasing hormone.

Simultaneous production of other human hormones such as follicle-stimulating hormone (abbreviated hFSH hereinafter) can also be carried out according to the present invention.

The hLH thus obtained can be collected easily by purification and separation techniques using conventional procedures such as salting-out, dialysis, filtration, centrifugation, concentration and lyophilization. If a further purified hLH preparation is desirable, a preparation of the highest purity can be obtained by the above mentioned techniques in combination with other conventional procedures such as adsorption and desorption with ion exchange, gel filtration, affinity chromatography, isoelectric point fractionation and electrophoresis.

The hLH preparation thus obtained can be advantageously usable alone or in combination with one or more agents for injection, external, internal or diagnostical administration in the prevention and treatment of human diseases.

Throughout the whole SPECIFICATION, the hLH production was determined by radio-immunoassay method as described in A. R. Midgley, Jr., Endocrinolgy, Vol. 79, pp. 10–18 (1966), and expressed by the International Unit (IU). Also, the simultaneous hFSH production was determined by radio-immunoassay method as described in C. Faiman, R. J. Ryan, J. Clin. Endocrinol. Metab., Vol. 27, pp. 444–447 (1967), and expressed by the International Unit (IU).

Several embodiments of the present invention are disclosed hereinafter.

EXAMPLE 1

Disaggregated human basophile adenoma cells, obtained by extracting from a patient suffering from basophile adenoma of the pituitary gland and mincing, were implanted subcutaneously in adult nude mice which were then fed in the usual way for four weeks. The resulting massive tumors, formed subcutaneously and about 10 g each were extracted and disaggregated by mincing and suspending in a physiological saline solution containing trypsin. After washing the cells with Earle's 199 medium (pH 7.2), supplemented with 10 v/v % foetal calf serum, the cells were resuspended to give a cell concentration of about $10^5$ cells per ml in a fresh preparation of the same medium which contained 30 mM L-arginine as the luteinizing hormone inducer, and incubated at 37° C. for about 15 hours to induce hLH. The cells were ultra-sonicated, and the hLH in the supernatant was determined. The hLH production was about 400 mIU per ml cell suspension. The simultaneous hFSH production in the supernatant was about 500 mIU per ml cell suspension.

Control cells, obtained by cultivating in vitro the human basophile adenoma cells in Earle's 199 medium (pH 7.2), supplemented with 10 v/v % foetal calf serum, and incubating at 37° C., were treated similarly as above to induce hLH. The hLH production was only about 70 mIU per ml cell suspension.

EXAMPLE 2

Disaggregated human basophile adenoma cells, obtained by extracting from a patient suffering from basophile adenoma of the pituitary gland and mincing, and a human leukemic lymphoblastoid line Namalwa were suspended together in a vessel to give a respective cell concentration of about $10^3$ cells per ml with a salt solution containing 140 mM NaCl, 54 mM KCl, 1 mM NaH$_2$PO$_4$ and 2 mM CaCl$_2$. The ice-chilled cell suspension was mixed with a fresh preparation of the same salt solution containing UV-irradiation preinactivated Sendai virus, transferred into a 37° C. incubator five minutes after the mixing, and stirred therein for 30 minutes to effect cell fusion, introducing the hLH producibility of the human basophile adenoma cells into the human leukemic lymphoblastoid line. After cloning according to conventional methods, the hybridoma cell strain capable of producing hLH was implanted intraperitoneally in adult nude mice which were then fed in the usual way for five weeks. The resulting massive tumors, about 15 g each, were extracted and treated similarly as in EXAMPLE 1 to induce hLH except that 30 mM L-arginine was replaced with about 10 mg luteinizing hormone releasing hormone. The hLH production was about 1,400 mIU per ml cell suspension.

The simultaneous hFSH production was about 1,600 mIU per ml cell suspension.

A control experiment was carried out similarly as in EXAMPLE 1 by cultivating in vitro the fused human leukemic lymphoblastoid line Namalwa, and exposing the multiplied human cells to the luteinizing hormone inducer. The hLH production was only about 90 mIU per ml cell suspension.

EXAMPLE 3

After injection of antiserum, prepared with rabbit according to conventional methods, into newborn hamsters, the animals were implanted subcutaneously with a human leukemic lymphoblastoid line JBL wherein the hLH producibility of the human basophile adenoma cells was introduced similarly as in EXAMPLE 2, and then fed in the usual way for three weeks. The resulting massive tumors formed subcutaneously and about 10 g each were extracted and treated similarly as in EXAMPLE 1 to induce hLH. The hLH production was about 1,300 mIU per ml cell suspension.

The simultaneous hFSH production was about 1,500 mIU per ml cell suspension.

A control experiment was carried out similarly as in EXAMPLE 1 by cultivating in vitro the fused human leukemic lymphoblastoid line JBL, and exposing the multiplied human cells to the luteinizing hormone inducer. The hLH production was only about 80 mIU per ml cell suspension.

EXAMPLE 4

Newborn rats were implanted intravenously with a human leukemic lymphoblastoid line Namalwa wherein the hLH producibility of the human basophile adenoma cells was introduced similarly as in EXAMPLE 2, and then fed in the usual way for four weeks. The resulting massive tumors, about 40 g each, were extracted and treated similarly as in EXAMPLE 2 to induce hLH. The hLH production was about 1,000 mIU per ml cell suspension.

A control experiment was carried out similarly as in EXAMPLE 1 by cultivating in vitro the fused human leukemic lymphoblastoid line Namalwa, and exposing the multiplied human cells to the luteinizing hormone inducer. The hLH production was only about 70 mIU per ml cell suspension.

EXAMPLE 5

After about 400 rem X-ray irradiation of adult mice to reduce their immunoreaction, the animals were implanted subcutaneously with human basophile adenoma cells, obtained similarly as in EXAMPLE 1, and then fed in the usual way for four weeks. The resulting massive tumors formed subcutaneously and about 15 g each were extracted and treated similarly as in EXAMPLE 2 to induce hLH. The hLH production was about 500 mIU per ml cell suspension.

A control experiment was carried out similarly as in EXAMPLE 1 by cultivating in vitro the human basophile adenoma cells, and exposing the multiplied human cells to the luteinizing hormone inducer. The hLH production was only about 50 mIU per ml cell suspension.

EXAMPLE 6

A human leukemic lymphoblastoid line JBL wherein the hLH producibility of the human basophile adenoma cells was introduced similarly as in EXAMPLE 3 was suspended in a physiological saline solution, and transferred into a plastic cylindrical diffusion chamber, inner volume about 10 ml, and equipped with a membrane filter having a pore size of about $0.5\mu$. After intraperitoneal embedding of the chamber into an adult rat, the animal was fed in the usual way for four weeks, and the chamber was removed. The human cell density in the chamber attained by the above operation was about $2 \times 10^9$ cells per ml which was about $10^3$-fold or more higher than that attained by in vitro cultivation using a $CO_2$ incubator. The human cells thus obtained were treated similarly as in EXAMPLE 2 to induce hLH. The hLH production was about 1,600 mIU per ml cell suspension.

The simultaneous hFSH production was about 1,300 mIU per ml cell suspension.

A control experiment was carried out similarly as in EXAMPLE 1 by cultivating in vitro the fused human leukemic lymphoblastoid line JBL, and exposing the multiplied human cells to the luteinizing hormone inducer. The hLH production was only about 80 mIU per ml cell suspension.

EXAMPLE 7

A human leukemic lymphoblastoid line JBL wherein the hLH producibility of the human basophile adenoma cells was introduced similarly as in EXAMPLE 3 was implanted into the allantoic cavities of embryonated eggs which had been preincubated at 37° C. for five days. After incubation of the embryonated eggs at this temperature for an additional one week, the multiplied human cells were harvested and treated similarly as in EXAMPLE 1 to induce hLH. The hLH production was about 1,200 mIU per ml cell suspension.

A control experiment was carried out similarly as in EXAMPLE 1 by cultivating in vitro the fused human leukemic lymphoblastoid line JBL, and exposing the multiplied human cells to the luteinizing hormone inducer. The hLH production was only about 80 mIU per ml cell suspension.

What we claim is:

1. A process for producing human luteinizing hormone (hLH), which comprises:
   (1) implanting human cells capable of producing hLH into a non-human warm-blooded animal;
   feeding the animal to cause the human cells therein to multiply;
   extracting and disaggregating the resultant multiplied human cells formed in the animal;
   culturing the human cells in a nutrient medium in the presence of a luteinizing hormone inducer for a period sufficient to accumulate a significant amount of hLH; and
   harvesting the accumulated hLH from the culture, or alternatively,
   (2) placing human cells capable of producing hLH in suspension in a diffusion chamber;
   embedding the chamber in or placing the chamber on a non-human warm-blooded animal in a manner such that the nutrient body fluid of the non-human warm-blooded animal is supplied to the cells within the chamber;
   feeding the animal to cause the human cells in the chamber to multiply;
   collecting the multiplied human cells from the chamber;
   culturing the human cells in a nutrient medium in the presence of a luteinizing hormone inducer for a period sufficient to accumulate a significant amount of hLH; and
   harvesting the accumulated hLH from the culture.

2. A process as set forth in claim 1, wherein said human cells capable of producing hLH are hybridoma cells derived by means of cell fusion of an established human lymphoblastoid line with human basophile adenoma cells.

3. A process as set forth in claim 2, wherein said established human lymphoblastoid line is a human leukemic lymphoblastoid line.

4. A process as set forth in claim 2, wherein said established human lymphoblastoid line is Namalwa or JBL.

5. A process as set forth in claim 2, wherein said hybridoma cells are derived by means of cell fusion using Sendai virus.

6. A process as set forth in claim 1, wherein said luteinizing hormone inducer is one or more members selected from the group consisting of amino acids, inorganic salts, and hormone.

7. A process as set forth in claim 1, wherein said non-human warm-blooded animal is a poultry or a mammalian.

8. A process as set forth in claim 1, wherein said luteinizing hormone inducer is one or more members selected from the group consisting of lysine, arginine, tryptophan, leucine, casamino acid, sodium chloride, potassium chloride, calcium chloride, magnesium sulfate, and luteinizing hormone releasing hormone.

9. A process as set forth in claim 1, wherein said non-human warmblooded animal is a chicken, pigeon, dog, cat, monkey, goat, pig, cow, horse, rabbit, guinea pig, rat, hamster, mouse or nude mouse.

* * * * *